(12) United States Patent
Cappello

(10) Patent No.: US 8,945,532 B2
(45) Date of Patent: Feb. 3, 2015

(54) ANTI-AGING FORMULATIONS

(71) Applicant: John V Cappello, King of Prussia, PA (US)

(72) Inventor: John V Cappello, King of Prussia, PA (US)

(*) Notice: Subject to any disclaimer, the term of this patent is extended or adjusted under 35 U.S.C. 154(b) by 18 days.

(21) Appl. No.: 13/723,503

(22) Filed: Dec. 21, 2012

(65) Prior Publication Data

US 2013/0115195 A1    May 9, 2013

Related U.S. Application Data

(63) Continuation-in-part of application No. 13/357,280, filed on Jan. 24, 2012.

(60) Provisional application No. 61/465,929, filed on Mar. 28, 2011.

(51) Int. Cl.

| | | |
|---|---|---|
| A61K 35/74 | (2006.01) | |
| A61K 31/715 | (2006.01) | |
| A61K 31/375 | (2006.01) | |
| A61K 31/357 | (2006.01) | |
| A61K 31/05 | (2006.01) | |
| A61K 31/223 | (2006.01) | |
| A61K 31/12 | (2006.01) | |
| A61K 31/737 | (2006.01) | |
| A61K 31/593 | (2006.01) | |
| A61K 31/137 | (2006.01) | |
| A61K 36/481 | (2006.01) | |
| A61K 38/16 | (2006.01) | |
| A61K 31/4172 | (2006.01) | |
| A23L 1/30 | (2006.01) | |
| A23L 1/337 | (2006.01) | |
| A61K 31/205 | (2006.01) | |
| A61K 31/7048 | (2006.01) | |

(52) U.S. Cl.
CPC ............. *A61K 38/164* (2013.01); *A61K 31/737* (2013.01); *A61K 35/748* (2013.01); *A61K 31/137* (2013.01); *A61K 31/12* (2013.01); *A61K 31/357* (2013.01); *A61K 31/05* (2013.01); *A61K 36/481* (2013.01); *A61K 31/4172* (2013.01); *A61K 31/593* (2013.01); *A61K 31/375* (2013.01); *A61K 31/223* (2013.01); *A61K 31/715* (2013.01); *A23L 1/3002* (2013.01); *A23L 1/337* (2013.01); *A61K 31/205* (2013.01); *A61K 31/7048* (2013.01); *A23V 2002/00* (2013.01)
USPC ...... 424/93.4; 424/93.51; 424/93.1; 514/18.7

(58) Field of Classification Search
None
See application file for complete search history.

(56) References Cited

U.S. PATENT DOCUMENTS

| | | | | |
|---|---|---|---|---|
| 7,473,427 | B2* | 1/2009 | Cappello | 424/195.17 |
| 2007/0065456 | A1* | 3/2007 | Woods | 424/195.17 |
| 2008/0248129 | A1* | 10/2008 | Bartunek et al. | 424/630 |
| 2010/0074969 | A1* | 3/2010 | Hughes et al. | 424/655 |

OTHER PUBLICATIONS

Cumashi, Albana; et al; "A comparative study of the anti-inflammatory, anticoagulant, antiangiogenic, and antiadhesive activities of nine different fucoidans from brown seaweeds" Glycobiology, 17, 541-552, 2007.*
Frenette PS, Weiss L., Using Fociodan for Stem Cell Mobilization, Medline,Oct. 1, 2000, 2460-8, 96(7), PubMed, USA.

* cited by examiner

*Primary Examiner* — Blaine Lankford
*Assistant Examiner* — David Berke-Schlessel
(74) *Attorney, Agent, or Firm* — Lawrence J. Shurupoff

(57) ABSTRACT

A dietary supplement based on fucoidan, blue-green algae, phycocyanin and phenylethylamine is fortified with one or more of curcumin, silymarin, resveratrol, *astragalus* root extract, astragoloside IV, vitamin D3, vitamin C, anhydrous trimethylglycine and brewers yeast to stimulate stem cell production and reduce the rate of telomere reduction or shortening. This can result in the repair of existing body cells and enhance longevity by stimulating the production of new stem cells and maintaining the telomeres on new stem cells as well as existing cells. The dietary supplement supports an increased life span by enhancing metabolic function, activating SIRT-1 anti-aging genes, and encouraging the production of new cells with longer telomeres.

4 Claims, No Drawings

ANTI-AGING FORMULATIONS

CROSS REFERENCE TO RELATED APPLICATIONS

This application is a continuation-in-part of U.S. application Ser. No. 13/357,280 filed Jan. 24, 2012 entitled Anti-Aging Formations which is incorporated herein in its entirety by reference and which claimed the benefit and priority of U.S. provisional application No. 61/465,929, entitled "Anti-Aging Formulations" filed Mar. 28, 2011.

BACKGROUND

Many attempts have been made to develop treatments and formulations to extend the human lifespan. To date, few, if any of these attempts have produced superior results, as few approaches fully recognize the basis or causes of aging. It is important to know the causes of aging, because as with treating a disease, one must first understand the problem, so that a precise remedy can be applied.

Some of the current theories of aging may be a result of other older conventional theories. Many of these theories are interlinked, in the same complex way that biological processes of the body and the many factors affecting these processes are interlinked.

Approaching any one or a combination of the following theories with a specialized treatment protocol may address and treat the aging problem on different levels, and help to slow down and eradicate some of the causes of aging. In order to appreciate the diversity of thought on the causes of aging, some of the current theories of aging are outlined below.

The DNA and Genetic Theories

Some scientists regard the DNA and genetic theories as planned obsolescence theories because they focus on the encoded programming within DNA. DNA is the blueprint of individual life obtained from one's parents. Humans are born with a unique code and a predetermined tendency to certain types of physical and mental functioning that regulate the rate at which one ages.

This type of genetic clock can be greatly influenced with regard to its rate of timing. For example, DNA is easily oxidized and this damage can be accumulated from diet, lifestyle, toxins, pollution, radiation and other outside influences. Thus, each individual has the ability to accelerate DNA damage or slow it down.

One recent theory regarding gene damage is the telomerase theory of aging. A telomere is the repetitive DNA sequence located at the end of a chromosome which shortens progressively with each cell division and limits the replicative potential of normal human somatic cells. It is now understood that telomeres, the sequences of nucleic acids extending from the ends of chromosomes, shorten every time a cell divides. This shortening of telomeres is believed to lead to cellular damage due to the inability of the cell to duplicate itself correctly. Each time a cell divides it duplicates itself a little less accurately or worse than the time before. This eventually leads to cellular dysfunction, aging and death.

Further research indicates that telomeres can be repaired by the introduction of a relevant hormone. Telomeres and their subsequent processes affect each other. Once we know what each telomere is responsible for, we may precisely introduce the necessary hormone and aid genetic repair, as well as hormonal balance.

Another key element in rebuilding the disappearing telomeres is the enzyme telomerase, an enzyme so far only found in germ and cancer cells. Telomerase appears to repair and replace telomeres helping to re-regulate the clock that controls the lifespan of dividing cells.

The Neuroendocrine Theory

This theory of aging elaborates on wear and tear by focusing on the neuroendocrine system. This system is a complicated network of biochemicals that govern the release of hormones which are altered by the walnut sized gland, the hypothalamus, located in the brain.

The Free Radical Theory

The term free radical describes any molecule that has a free electron. This property makes the free radical molecule react with healthy molecules in a destructive way. Because the free radical molecule has an extra electron, it creates an extra negative charge. This unbalanced energy makes the free radical bind itself to another balanced molecule. In so doing, the balanced molecule becomes unbalanced and thus a free radical itself. It is known that diet, lifestyle, drugs (e.g. tobacco and alcohol) and radiation are all accelerators of free radical production within the body and can influence the rate of aging.

The Membrane Theory of Aging

According to this theory, it is the age-related changes of the cells' ability to transfer chemicals, heat and electrical processes that impair the integrity of the cells.

As one grows older the cell membrane becomes less lipid, less watery and more solid. This impedes its efficiency to conduct normal cell functions. In particular, this can lead to a toxic accumulation within the cell. This cellular toxin is referred to as lipofuscin and as one grows older lipofuscin deposits become more present in the brain, heart and lungs and also in the skin. Some of the skin age-pigments referred to as liver spots or age spots are composed of lipofuscin. It is known that Alzheimer disease patients have much higher levels of lipofuscin deposits than compared to their healthy control groups. The cells' declining efficiency also means that the essential and regular transfer of sodium and potassium is impaired, thus reducing cellular communication. It is also believed that electrical conduction and heat transfer is also impaired by this cellular degradation.

The Hayflick Limit Theory

The Hayflick Limit Theory of aging suggests that the human cell is limited in the number of times it can divide. Part of this theory may be affected by cell waste accumulation (which is described in the Membrane Theory of aging). It is theorized that the human cell's ability to divide is limited to approximately 50 times, after which it simply stops dividing (and hence dies). It has been shown that nutrition has an effect on cells, with overfed cells dividing much faster than underfed cells. As cells divide to help repair and regenerate themselves the DNA & Genetic Theory of Aging may play a role. Each time a cell divides it may lose some blue-print information. Eventually (after 50-odd times of division) there is simply not enough DNA information available to complete any sort of division.

The Mitochondrial Decline Theory

The mitochondria are the power producing organelles found in every cell of every organ. Their primary job is to create adenosine triphosphate (ATP). They do so in the various energy cycles that involve nutrients such as acetyl-L-carnitine, CoQ10 (idebenone), NADH and some B vitamins. As the mitochondria decline, aging increases.

The Cross-Linking Theory

The Cross-Linking Theory of aging is also referred to as the glycosylation theory of aging. In this theory, it is the binding of glucose (simple sugars) to protein, (a process that occurs under the presence of oxygen) that causes various aging problems. Once this binding has occurred, the protein becomes impaired and is unable to perform as efficiently. Living a longer life leads to the increased possibility of oxygen meeting glucose and binding glucose to protein. This can lead to cross-linking disorders including senile cataracts and the appearance of tough, leathery and yellow skin.

SUMMARY

In accordance with this disclosure, a new approach to slowing aging and increasing longevity is to both increase the number of healthy cells in the human body and to increase the length of the telomeres in the DNA of these healthy cells. Telomeres in existing cells can be lengthened and the length of telomeres in newly produced stem cells can be increased with the daily administration of the dual-purpose formulations disclosed below. These results can be accomplished by increasing the number of new circulating adult stem cells which are responsible for the natural rebuilding process of the body, with the dietary supplements discussed below.

Additional dietary supplements are disclosed which decrease the loss of telomeres as well as repair those telomeres in the process of being lost. This new approach to life enhancement builds on prior improvements set forth in U.S. Pat. No. 7,473,427, which is incorporated herein in its entirety by reference. The compositions and dietary supplements described below support increased life span by enhancing metabolic function and activating SIRT-1 (silent information regulator type 1) anti-aging genes and encouraging the production of new cells with longer telomeres.

As one ages, telomere length decreases. By encouraging or stimulating telomere lengthening with nutritional supplementation, one may attain an increased or maximum lifespan with less debilitation in advancing years. The nutritional supplements when combined as described below may repair telomere shortening and decrease the rate of telomere shortening.

A decrease in telomere length has been associated with aging. Likewise, susceptibility to many degenerative diseases also increases as telomere length decreases. The nutritional supplements disclosed herein aid in nourishing and producing an increased amount of adult stem cells in circulation. These new adult stem cells are believed to replace old cells with newer cells having longer telomeres on their chromosomes. The dietary nutritional supplements disclosed below support telomere lengthening to aid in attaining a maximum life span with the least debilitation in advancing years, as well as repair telomere shortening and decrease the rate of telomere shortening.

DESCRIPTION OF REPRESENTATIVE EMBODIMENTS

As disclosed in U.S. Pat. No. 7,473,427, blue-green algae provides the essential vitamins, minerals, proteins and nutrients required to support life. One form of blue-green algae known as *aphanizomenon flos-aqua* (AFA) is particularly effective in stimulating natural stem cell production within the body. Stem cells not only combat disease, they contribute to health maintenance and reduce the effects of injury and aging.

As further described in U.S. Pat. No. 7,473,427, by combining phycocyanin with AFA, inflammation such as caused by injury, arthritis or irritants can be reduced or prevented. Phycocyanin can be extracted from AFA and provided as a supplement to AFA. Alternatively, phycocyanin can be provided in the form of *arthrospira platentis*. While phycocyanin is available in the form of an extract of AFA, phycocyanin can also be provided in the less expensive form of *arthrospira platentis*, which contains about 19% to 20% of phycocyanin. Phenylethylamine (PEA) such as in the form of PEA hydrochloride, can also be combined with AFA to reduce depression and promote alertness.

The combination of at least about 250 mg of whole blue-green algae, such as AFA, at least about 25 mg of phycocyanin and at least about 0.35 mg of phenylethylamine supports an increased life span by enhancing the metabolic function and activation of SIRT-1 anti-aging genes. This in turn encourages the production of new cells with longer telomeres. It is believed this combination can repair shortened telomeres as well as decrease the rate of telomere shortening in both new and existing cells.

The combination of whole blue-green algae (such as AFA), with phenylethylamine (PEA) and phycocyanin aids in nourishing and increasing the production of adult stem cells in circulation. These newly produced stem cells can replace older cells in the body with newer cells having longer telomeres on their chromosomes. This resists the aging process which has been associated with a decrease in telomere length.

While the combination of whole blue-green algae, PEA and phycocyanin provides an effective primary or base composition for stimulating stem cell production, the ingredients in this primary composition can be made more effective in stimulating stem cell production with the addition of one or more of the ingredients disclosed below. That is, it has been found that by supplementing this primary composition with one or more additional ingredients, the amount of stem cell production and the degree of anti-aging can be significantly improved. The result is a life-extending dietary supplement that not only retards the aging process but also repairs prior damage to existing cells.

Anti-aging and body repair can be improved by adding the anti-oxidant curcumin to the primary composition of whole blue-green algae (such as AFA), PEA and phycocyanin. Curcumin contains high levels of polyphenols and is available as a 95% standardized extract of *curcuma longa* also known as the spice turmeric, a member of the ginger root family. Curcumin can be added to the primary composition alone, or with one or more of the additional ingredients identified below.

Curcumin is the principal curcuminoid of turmeric. Fifty milligrams of 95% standardized curcumin extract provides the equivalent amount of curcuminoids obtained by eating up to two grams of the spice turmeric. Health and anti-aging benefits are associated with curcumin. Studies have been conducted regarding a link between curcumin and mTOR (mammalian target of rapamycin) inhibition. The inhibition of mTOR is beneficial as it limits a tumor's ability to grow and spread.

Another beneficial additive is silymarin, which works to stabilize liver cell membranes and acts as an antioxidant to protect liver cells from free radical damage. Added to the base or primary composition of whole blue-green algae, PEA and phycocyanin, alone or with one or more of the other additives discussed herein, silymarin helps to regenerate healthy liver cells.

Another anti-aging ingredient is resveratrol, available as a 98% trans isomer. Resveratrol is believed to activate the SIRT-1 anti-aging gene and enhance the beneficial anti-aging effects of the primary composition when added to the base or primary composition singularly or in combination with any one or more of the other additives described herein.

*Astragalus* root includes a chemical that prevents or slows progressive telomere shortening, reduces DNA damage and assists in the ability to repair DNA. Moreover, *astragalus* root typically includes about 20% by weight of polysaccharides which possess an additional anti-aging effect related to the anti-oxidative properties of polysaccharides. In addition, the polysaccharides in *astragalus* act as a transport medium for astragoloside IV, thereby increasing its beneficial effect.

Another effective anti-aging ingredient is astragoloside IV which is believed to be a telomerase activator. It is a component of *astragalus* known to repair bits of telomeres. By activating the enzyme telomerase, the short bits of DNA forming telomeres can be replaced. Astragoloside IV can be added to the primary composition alone or in combination with one or more of the other ingredients disclosed herein.

Still another anti-aging ingredient is L-carnosine, a naturally occurring dipeptide, which can oppose age-related glycolation. L-carnosine also appears to reduce the rate at which telomeres shorten and delay replicative cellular senescence and extend the lifespan of human cells. Added alone or with any one or more of the other ingredients to the primary composition, L-carnosine provides beneficial anti-aging properties.

The length of telomeres on leukocytes or "white blood cells" (LTL) is a predictor of age-related diseases. The length of these telomeres decreases with cell division and with increased inflammation. Vitamin D3 is a potent inhibitor of the inflammatory response and reduces the turnover of leukocytes. Studies have associated higher serum vitamin D3 levels with lower telomeric aging and increased stem cell circulation. Adding vitamin D3 to the primary composition alone or in combination with one or more of the other ingredients disclosed herein preserves LTL and thereby slows aging. Vitamin D3 can enhance both telomere length and improve adult stem cell circulation. Vitamin D3 also stimulates the activation of dormant adult stem cells in the bone marrow, leading to improved stem cell production. While the minimum daily requirement (MDR) of 400 IU of vitamin D3 is standard or common, 250 IU to 5000 IU (6.25 mcg to 125 mcg) of vitamin D3 and preferably 250 to 2000 IU (6.25 mcg to 50 mcg) of vitamin D3 can be taken in combination with the primary or base formulation, alone or with any one or more of the other ingredients disclosed herein.

Vitamin C can be added to the base or primary formulation alone or in combination with one or more of the other ingredients disclosed herein. Vitamin C increases the differentiating abilities of adult stem cells. Vitamin C can be added to the primary formulation in the amount of 15 mg to 60 mg per dosage.

Trimethylglycine (TMG) in an anhydrous form increases absorption from the digestive tract into the bloodstream of most dietary supplements including those disclosed herein. Trimethylglycine also functions as a methyl donor. Adding 0.5 to 15 mg of TMG to the primary composition alone or with any other ingredient disclosed herein increases the effectiveness and efficiency of the formulations.

EXAMPLE

One representative anti-aging formulation of a beneficial dietary supplement for enhancing stem cell formation, slowing the aging process and repairing damaged cells includes:
250 mg of whole blue-green algae, such as *aphanizomenon flos aqua* (AFA);
170 mg of *arthrospira platentis* containing 19% to 20% phycocyanin, or an equivalent amount of phycocyanin extract (e.g. up to 25 mg or more).
For purposes of definition, the ingredients listed below are defined collectively as a "Telomere Blend", and are added to the AFA and phycocyanin (or *arthrospira platentis*) listed immediately above for the purpose of repairing and maintaining telomere length and supporting and protecting newly produced cells.
50 mg of curcumin (in the form of 95% standardized extract)
50 mg silymarin
50 mg resveratrol
50 mg *astragalus* root extract (20% polysaccharides)
50 mg astragoloside IV
50 mg L-carnosine
30 mg. Vitamin C
25 mg phenylethylamine
5 mg anhydrous trimethylglycine (optional)
500 IU (12.5 mcg) Vitamin D3

The above composition can be provided in a 750 mg gelatin capsule. The amount of each ingredient can vary widely within the ranges noted below.

Whole AFA—250 mg to 750 mg; phycocyanin—25 mg to 100 mg extract or 125 mg to 500 mg of *arthrospira platentis* at 19% to 20% by weight of phycocyanin; curcumin—95% standardized extract—5 mg to 150 mg; silymarin—5 mg to 150 mg; resveratrol (98%)—5 mg to 150 mg; astragoloside IV—5 mg to 150 mg; L-carnosine—5 mg to 150 mg; phenylethylamine—2.5 mg to 75 mg; anhydrous trimethylglycine—0.5 mg to 15 mg. This formulation can be further enhanced with the addition of 250 to 5000 IU (6.25 mcg to 125 mcg) of Vitamin D3 and 15 to 60 mg of vitamin C.

While there are some formulations available for increasing stem cell production and others for telomere and genetic modifications, none is known which does both as described herein. The multiple-action formulation disclosed herein may be provided in a capsule, as a tablet or liquid for daily introduction into the human digestive tract. When provided in the 750 mg capsules described above, two capsules can be taken daily, such as one capsule in the morning and one capsule in the evening. However, at least one capsule should be taken daily to achieve the results described above.

It should be noted that each of the ingredients in the 750 mg formulation set forth above serves to retard aging or to enhance the anti-aging effect of one or more of the other ingredients. Any combination of the primary formulation of AFA, PEA and phycocyanin with one or more of the ingredients listed above can provide an anti-aging effect and promote body repair.

The combination of whole *Aphanizomenon Flos Aqua* (AFA), phycocyanin (such as in the form of *Arthrospira platentis*) and phenylethylamine (PEA) provides a base or primary composition ("primary") that promotes the human body's production of new stem cells. The remaining ingredients facilitate and enhance the repair and remediation of both new and old (existing) cells, and in particular, adult stem cells.

The efficacy of the primary formulation is improved by the addition of any one or more of the additional ingredient listed in 750 mg composition identified above. New stem cells with a full complement of telomeres are produced by the base composition and are protected against telomere shortening by any one or more of the remaining ingredients. These remaining ingredients also slow down the shortening of telomeres on existing cells so as to slow down the aging process.

An additional ingredient to the Telomere Blend as well as to the combination of the Telomere Blend with whole *Aphanizomenon Flos Aqua* (AFA) and phycocyanin (such as in the form of *Arthrospira platentis*) is 150 mg to 250 mg. or more of saccharomyces cerevisiae, the scientific name for brewer's yeast. Such an addition whether in capsule, tablet, solution or suspension would provide much needed trace amounts of RNA and DNA to the body for added potential anti-aging effect. Brewer's yeast can be added to the base or primary composition alone or in combination with one or more of the other ingredients note above. The Telomere Blend can be provided as a separate "stand alone" formulation to be used alone or as a supplement to be taken with any other anti-aging or supplement formulation to enhance telomere length.

As disclosed in U.S. Pat. No. 7,473,427 noted above, polscaccharides aid in the transport of PEA and phycocyanin through the digestive tract and into the blood. This is important not only from a simple efficiency perspective, but also from an economic perspective.

Because PEA and phycocyanin occur naturally in blue-green algae in relatively small amounts, large amounts of blue-green algae must be processed to extract PEA and phycocyanin. This makes PEA and phycocyanin extracts very expensive. By improving the transport of PEA and phycocyanin into the bloodstream by combining them with whole AFA, smaller amounts of these components are required to be ingested in order to produce the same therapeutic effects as those achieved with larger amounts of PEA and phycocyanin taken without whole AFA. This improved transport is largely attributable to the polysaccharides present in whole blue-green algae.

The amount of polysaccharide in blue-green algae, such as AFA, is typically around 20% by weight. As relatively large amounts of blue-green algae are required to achieve an effective amount of polysaccharide for improving transport of PEA and phycocyanin into the bloodstream, it would be advantageous to provide an economical supplemental or substitute source of polysaccharides in order to reduce or eliminate the need for relatively large amounts of blue-green algae.

A supplemental or substitute source of blue-green algae is also beneficial insofar as the current sources of blue-green algae, such as AFA, that are grown in the wild (predominantly in the USA in the Klamath Lake region of Oregon), are dependent upon the vagaries of nature for harvesting, resulting in an uncertain supply.

In order to provide a more economical and widely available source of polysaccharides while at the same time improving the ability of stem cells to replace dead cells, it has been found that a sulfated polysaccharide found mainly in the various species of brown seaweed meets these requirements. More particularly, fucoidan, a sulfated polysaccharide, is derived from brown seaweed such as kombu, limu moui, bladderwrack, wakame, mozuku and hijki.

There are numerous commercial sources of fucoidan. One source of fucoidan which meets the needs noted above is available through FMC Biopolymer sold under the brand "ProtaSea". This source of fucoidan is obtained from a regulated and sustainable wild harvest of seaweed from the genus laminaria, species hyperborean. It is not genetically modified and is free of bovine spongiform encephalopatly and transmissible spongiform encephalopathy.

An advantage of fucoidan is that it can act as either a dilutant or total replacement for the blue-green algae and AFA in the formulations described above. Whereas whole AFA contains around 20% by weight of polysaccharide, fucoidan typically contains around 60% by weight of polysaccharide. That means that a smaller amount by weight and volume of fucoidan, typically ⅓ the amount by weight and volume of blue-green algae, can supply the same amount of polysaccharide as that supplied by whole blue-green algae, such as AFA. As discussed below, this weight and volume advantage of fucoidan provides a practical advantage when providing the formulations described herein in capsules or tablets for oral ingestion.

Another advantage to the increased amount or concentration of polysaachairdes provided by fucoidan is fucoidan's ability to aid in the transport into the blood of orally administered curcumin, silymarin, resveratol, astragoloside IV, L-caruosine and trimethylglycine (TMG). Other advantages of fucoidan include improving joint flexibility and lubrication, supporting healthy immune systems, assisting in maintaining good cholesterol levels, supporting healthy cell growth, supporting the circulatory system, improving digestive health and promoting firm and healthy skin.

Of significant benefit of supplementing blue-green algae with fucoidan or substituting fucoidan completely for blue-green algae in the formulations disclosed herein is the ability of fucoidan to enhance and promote an increase in the circulation of adult stem cells and progenitor cells from the bone marrow. Fucoidan can either be combined with blue-green algae as a supplement or added as a dilutant wherein the amount of blue-green algae can be reduced while still maintaining stem cell simulation and polysaccharide transport at desired levels.

As noted above, fucoidan can replace some or all of the blue-green algae, such as MA, provided in the formulations described above. When fucoidan replaces same or all of the blue-green algae, the same amount of polysaccharides may be provided in a smaller volume as compared to using only blue-green algae. This provides a desirable practical advantage by allowing for an increase of other ingredients or constituents in the formulation while maintaining the same volume of overall formulation with the same volume of polysaccharides.

As many people do not enjoy swallowing large pills or capsules, nor enjoy taking many pills or capsules at one time, the flexibility in reducing the amount of blue-green algae and increasing the amount of other ingredients through the substitution of fucoidan for some or all of the blue-green algae, allows for the addition of new constituents or increased amounts of current constituents, while maintaining the same size pill or capsule.

For example, 250 mg of whole AFA contains about 50 mg of polysaccharides, 500 mg of whole AFA contains about 100 mg of polysaccharides and 750 mg of whole AFA contains about 150 mg of polysaccharides. To obtain the same amounts of polysaccharides, a much lower volume and weight of fucoidan can be used. That is, to obtain 50 mg of polysaccharides, only about 90 mg of fucoidan is required. To obtain 100 mg of polysaccharides, about 180 mg of fucoidan is required, and to obtain 150 mg of polysaccharides, only about 250 mg of fucoidan is required.

In order to formulate a commercially economical and useful product which can be reasonably comfortably administered orally, an "00 capsule" also known as a "double 0 capsule" can be used to contain about 750 mg of ingredients. It is therefore desirable to limit a formulation to about 750 mg so that the formulation can be provided in one or more 00 capsules for ease of swallowing.

By way of example, should one wish to provide a dietary formulation containing only polysaccharides and phycocyanin as the active ingredients in a 00 capsule, one could combine blue-green algae in the form of AFA with *Arthrospira platensis* (AP) or alternatively one could combine fucoidan with AP. AP is one of the most economical sources of phycocyanin but contains only a maximum of about 20% by weight of phycocyanin. This necessitates a large amount of AP to obtain desired effective amounts of phycocyanin.

Because phycocyanin is one of the most active and beneficial ingredients in the formulations disclosed herein, it is desirable to use a relatively large amount of phycocyanin, but keep the overall formulation dosage within a 750 mg limit to accommodate use of a 00 capsule for ease of swallowing.

If one wanted a dosage of 130 mg of phycocyanin with the remainder being fucoidan, one would use 650 mg of high yield AP (typically 20% maximum by weight phycocyanin) and 100 mg of fucoidan providing 60 mg of polysaccharides as well as providing the health benefits and stem cell production noted above while acting as a digestive transport aid to phycocyanin (and any other optional ingredients). That is, the polysaccharides in fucoidan increase the amount of phycocyanin transported from the digestive system into the bloodstream. When fucoidan provides at least some of the polysaccharides in the formulation, an additional benefit results in the form of enhanced stem cell production and circulation.

To provide the same 60 mg of polysaccharides with AFA, (typically only about 20% by weight and volume of polysaccharides) 300 mg of AFA is needed. This leaves only 450 mg available for AP in a 750 mg capsule which amounts to only about 90 mg of phycocyanin, compared to the 130 mg of phycocyanin when using fucoidan. Even greater benefits of the formulations disclosed herein can be obtained with the production of compressed tablets that can be produced up to 900 mg in total content.

Fucoidan can be substitued in whole or in part for blue-green algae and/or AFA in any of the formulation disclosed above. It can replace or be combined in any amounts with blue-green algae and/or AFA. Fucoidan provides increased amounts of phycocyanin in any given volume or weight of formulation as compared to whole AFA and can serve as a basis for any anti-aging formulation.

As noted above, a dietary composition for stimulating the rapid mobilization of stem cells while reducing inflammation in the human body can include fucoidan and phycocyanin. Fucoidan can be provided in effective single capsule or single tablet amounts sufficient to include at least about 50 mg of polysaccharides and up to about 250 mg of polysaccharides or more. This equates to about 90 mg to about 450 mg of fucoidan. Of course, less fucoidan can be provided as long as additional polysaccharides are provided such as by the addition of blue-green algae.

Phycocyanin should be provided in an amount of at least about 25 mg up to about 600 mg per capsule or tablet. This can be provided as an extract of AFA or in the form of Arthrospire platensis. While an effective composition of only fucoidan and/or blue-green algae and phycocyanin is contemplated, the addition of phenylethylamine (PEA) in an effective amount of at least about 35 mg can reduce depression and produce elevated moods by enhancing dopamine and norepinephrine in the brain. The upper limits of each ingredient are, in one embodiment, set by the volume of one or more 750 mg geletion capsules or 900 mg tablets. More than one capsule or tablet may be taken orally at one time, but a suggested dosage is two 750 mg geletin capsules or two 900 mg tablets.

The base formulation of fucoidan (brown sea weed) and phycocyanin and the base formulation of fucoidan, phycocyanin and PEA can be enhanced with any one or more of curcumin, silymarin, resveratol, astragoliside IV. L-carnosine and trimethylglycine (TMG).

Additional benefits can be achieved with the addition of one or more vitamins and/or minerals such as provided in commercially available multivitamins and minerals.

When formulating a base composition which includes fucoidan and phycocyanin, the relative amounts, by weight, of each base component can range from about 10% to about 90% fucoidan and about 10% to about 90% phycocyanin with the combined weights of fucoidan and phycocyanin being equal to about 100% by weight of these two components without regard to any additional components. A preferred range is about 40% to about 60% by weight of fucoidan and about 40% to about 60% by weight of phycocyanin with the sum of the weights of fucoidan and phycocyanin adding up to 100%, without regard to any additional ingredients.

There has been disclosed the best embodiment of the dietary supplement and method of use presently contemplated. Numerous modifications and variations of the supplement are possible in light of the above teachings. It is therefore to be understood that within the scope of the appended claims, the invention may be practiced otherwise than as specifically described herein. For example, the base or primary composition can be enhanced by the addition of any one ingredient or any combination of two, three, four, five or more ingredients noted above. Each ingredient provides an incremental improvement in telomere production and/or telomere maintenance.

What is claimed is:

1. A dietary supplement in capsule or tablet form for oral ingestion and promoting longevity by stimulating stem cell production and stem cell circulation and reducing the rate of telomere shortening, comprising:
    50 to 150 mg fucoidan stimulating said stem cell circulation;
    25 to 100 mg phycocyanin reducing inflammation;
    5 to 150 mg curcumin provided as a standard extract of *curcuma longa* limiting tumor growth and providing polyphenols;
    5 to 150 mg silymarin protecting liver cells;
    5 to 150 mg resveratrol in the form of a 98% transisomer activating anti-aging genes;
    5 to 150 mg astragoloside IV;
    5 to 150 mg L-carnosine reducing the rate of said telomere shortening;
    250 to 5000 IU (6.25 mcg to 125 mcg) vitamin D3 increasing telomere length and improving said stem cell circulation;
    15 to 60 mg vitamin C increasing the ability of adult stem cells to differentiate;
    0.5 to 15 mg anhydrous trimethylglycine serving as a methyl donor; and
    2.5 to 75 mg phenylethylamine hydrochloride reducing depression and promoting alertness; and
    150 to 250 mg saccharomyces cerevisiae providing RNA and DNA for anti-aging effect.

2. The dietary supplement of claim 1, further comprising whole blue-green algae.

3. The dietary supplement of claim 1, wherein said fucoidan is provided in the form of brown seaweed.

4. The dietary supplement of claim 1 wherein said phycocyanin is provided as 125 to 500 mg of *Arthrospira platensis* comprising about 19 to 20% by weight of said phycocyanin.

* * * * *